United States Patent [19]

Unami et al.

[11] Patent Number: 4,998,043
[45] Date of Patent: Mar. 5, 1991

[54] LED STABILIZING LIGHT SOURCE DEVICE

[75] Inventors: Yoshihara Unami, Tomisato; Masao Tanaka, Yachiyo, both of Japan

[73] Assignee: Fujikura Ltd., Tokyo, Japan

[21] Appl. No.: 345,883

[22] Filed: May 1, 1989

[51] Int. Cl.⁵ .............................................. G01J 1/32
[52] U.S. Cl. ..................................... 315/151; 250/205
[58] Field of Search ........................ 315/151; 250/205

[56] References Cited

U.S. PATENT DOCUMENTS

| | | | |
|---|---|---|---|
| 3,770,966 | 11/1973 | Sagawa et al. | 250/205 |
| 3,996,494 | 12/1976 | Suga | 315/151 |
| 4,182,977 | 1/1980 | Stricklin, Jr. | 315/151 X |
| 4,281,245 | 7/1981 | Brogardh et al. | 250/205 X |
| 4,687,919 | 8/1987 | Nagano | 315/151 X |

FOREIGN PATENT DOCUMENTS 63-46784  2/1988  Japan .

OTHER PUBLICATIONS

Thomas et al., Digital Feedback Light-Emitting Diode Control, IBM Technical Disclosure Bulletin, vol. 16, No. 8, Jan. 1974, pp. 2598-2600.
National Conference Record, 1986, The Institute of Electronics and Communication Engineers of Japan. (part 2).

Primary Examiner—Robert J. Pascal
Attorney, Agent, or Firm—Frishauf, Holtz, Goodman & Woodward

[57] ABSTRACT

An LED stabilizing light source device comprises an LED, a drive circuit for driving the LED, a wavelength filter for filtering the light emitted from the LED, a light splitter for splitting the light passing through the filter, a photodiode for receiving the split light. The device further comprises a feedback loop for feeding an output of the photodiode to the drive circuit.

5 Claims, 3 Drawing Sheets

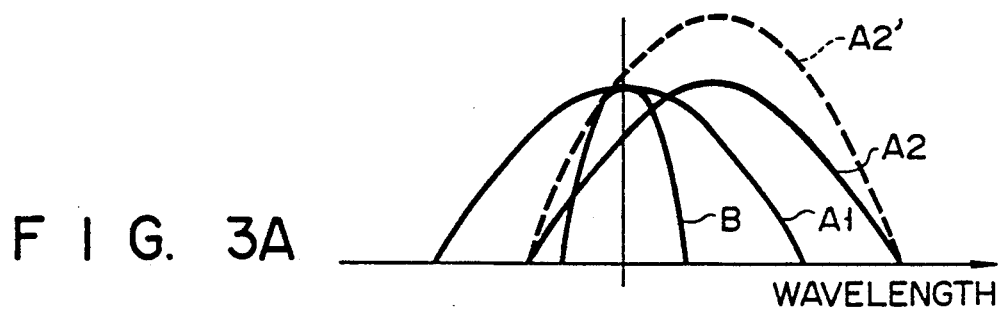
F I G. 3A
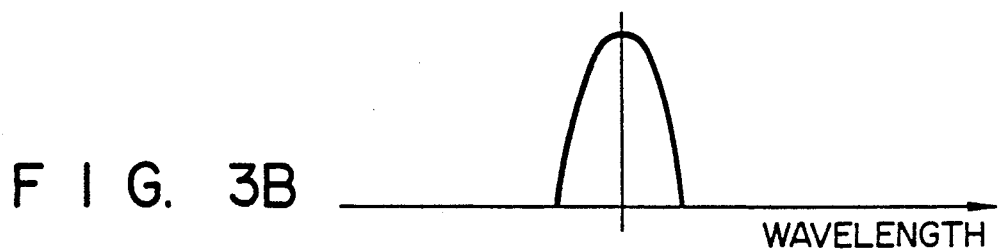
F I G. 3B
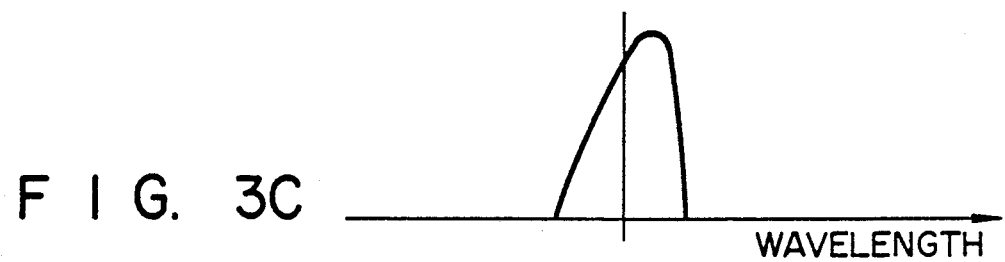
F I G. 3C
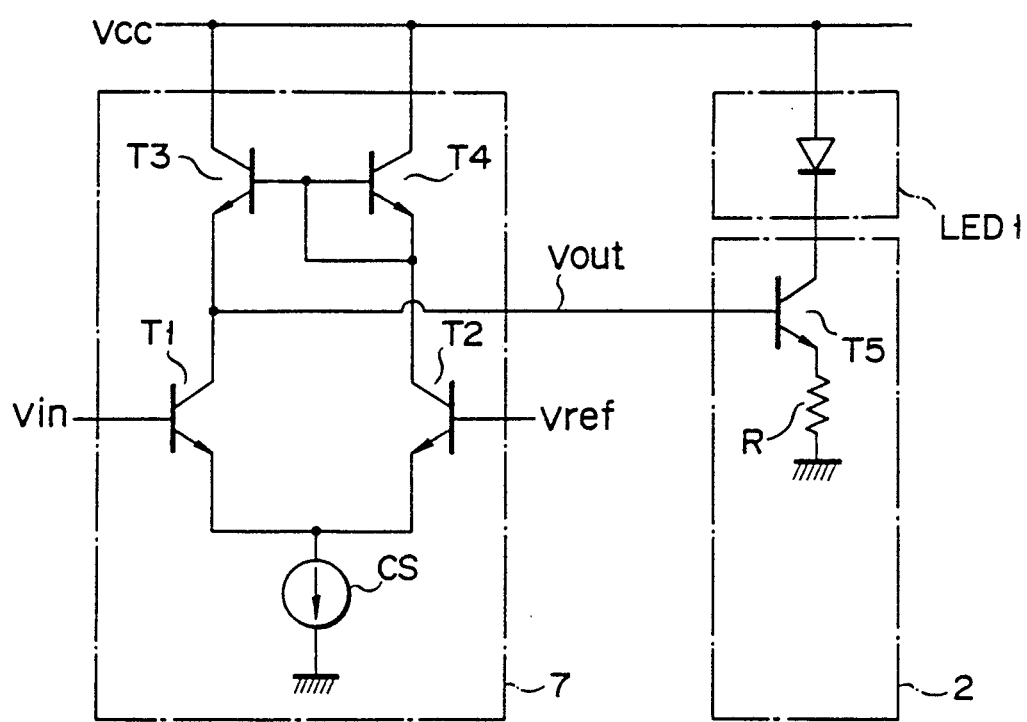
F I G. 4

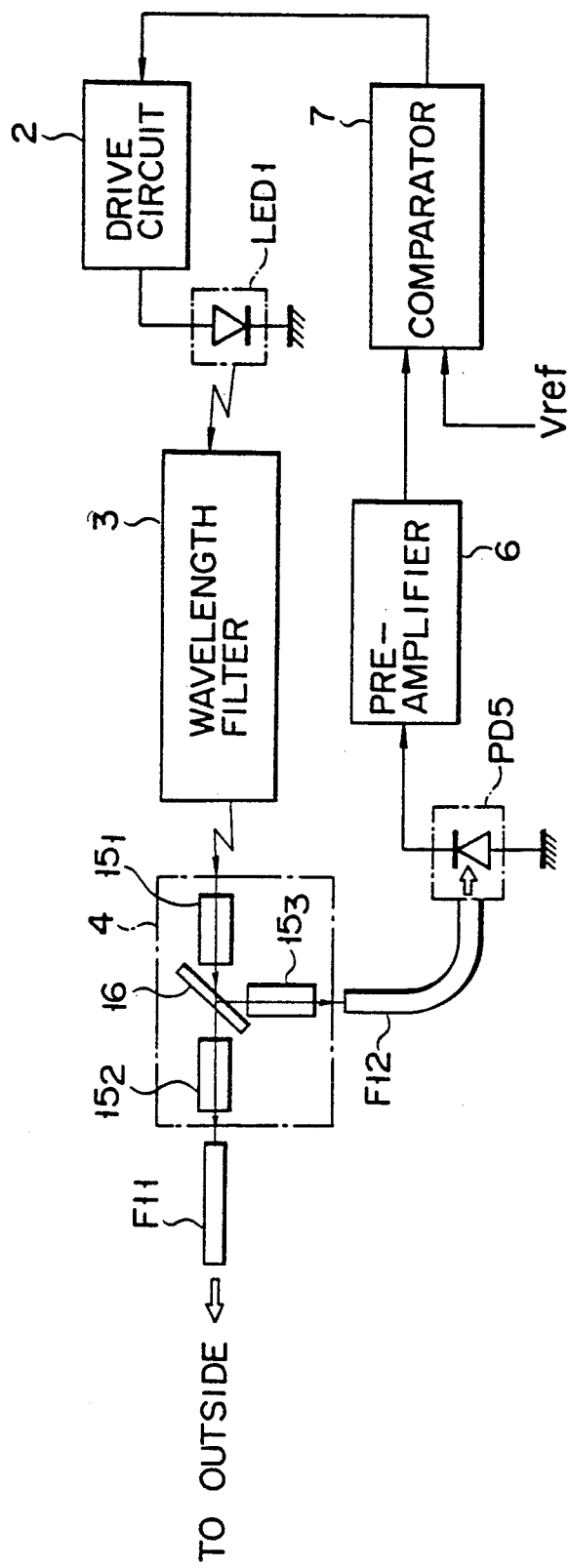
F I G. 5

LED STABILIZING LIGHT SOURCE DEVICE

BACKGROUND OF THE INVENTION

1. Field of the Invention

The present invention relates to an LED (Light-Emitting Diode) stabilizing light source device suitable for measurement of light propagation characteristics of an optical fiber.

2. Description of the Related Art

When the ambient temperature of an LED serving as a light-emitting element changes, output light therefrom also changes. Therefore, conventionally, the ambient temperature of the LED is measured using a heat-sensitive element such as a thermistor, and an output from a drive circuit for driving the LED is controlled in accordance with the sensed temperature, thus stabilizing the output light from the LED.

In the above conventional system, however, it generally takes several tens of minutes until the output light is stabilized after a power switch is turned on.

Since, furthermore, the temperature characteristics of LEDs are generally different, each LED requires a thermistor suitable to the LED. However, the temperature characteristics of LEDs and thermistors are generally not the same, thus an error will occur between the temperature characteristics. Therefore, it is required to compensate for the error to control the driving of the LEDs with high precision. However, this is troublesome and lowers the operability of the device.

SUMMARY OF THE INVENTION

The present invention has been made in consideration of the above situations, and has as its object to provide an LED stabilizing light source device which has a high operability, and starts to operate in a short time from the power-on of the device.

According to the present invention, there is provided an LED stabilizing light source device comprising an LED, a drive circuit for driving said LED, a wavelength filter having a predetermined passing band, for receiving output light from said LED, and passing therethrough a portion of the light whose wavelength is within said predetermined passing band, a light splitter for splitting a beam of the light passing through said wavelength filter, a beam guide member for guiding one split beam to the outside of the light source, a beam receiving member for receiving the other split beam, and outputting a signal corresponding to the intensity of said other split beam, and a feedback loop for feeding back an output from said beam receiving member to said drive circuit.

BRIEF DESCRIPTION OF THE DRAWINGS

FIGS. 3A to 3C are graphs showing the spectral characteristics of light as in FIGS. 2A to 2C;

FIG. 4 is a circuit diagram showing an arrangement of a comparator and a drive circuit in the device shown in FIG. 1; and FIG. 5 is a block diagram of an LED stabilizing light source device according to another embodiment of the present invention.

DETAILED DESCRIPTION OF THE PREFERRED EMBODIMENTS

Figure 1:
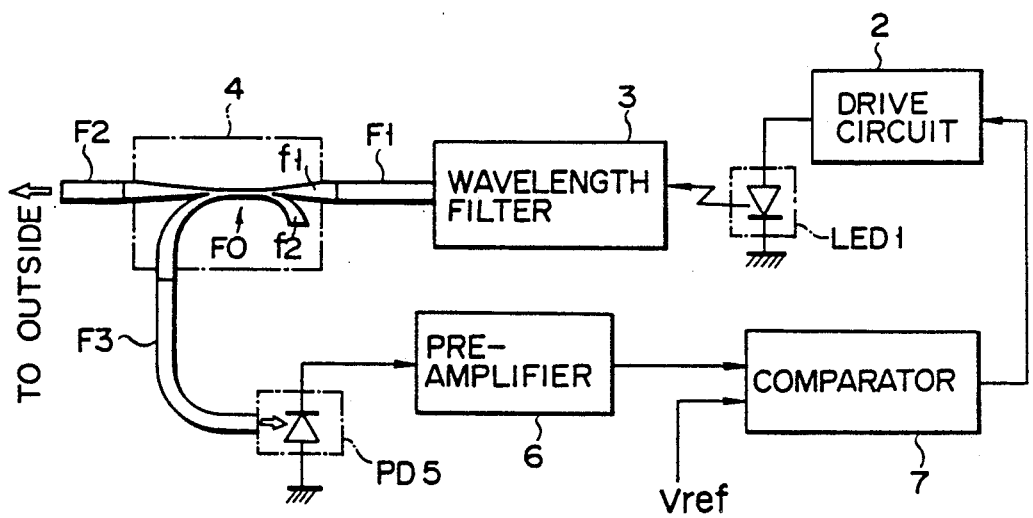
FIG. 1 is a block diagram of an LED stabilizing light source device according to an embodiment of the present invention.

In FIG. 1, an LED 1 receives a drive current from a drive circuit 2 and emits light having an intensity corresponding to the magnitude of the drive current. The emitted light is input to a band-pass wavelength filter or band-pass color filter 3 having a predetermined passing band of wavelength, and a portion of the light whose wavelength is within the passing band of the filter 3 passes via the filter 3. The light portion is input to an optical fiber F0 of a fiber coupler or light splitter 4 via an optical fiber F1 of the same type as the optical fiber F0, to split the light portion into two light beams. The optical fiber F0 is formed of two optical fibers f1 and f2 of the same type. One split beam is guided to the outside via an optical fiber F2 which is the same type as the optical fibers F0 and F1. The other split beam is input to a photodiode PD5 serving as a light-receiving element via an optical fiber F3 which is the same type as the optical fibers F0, F1, and F2. A current corresponding to the intensity of the input beam flows through the photodiode PD5 into a pre-amplifier 6. A voltage corresponding to the current is output from the preamplifier 6. The output voltage is input to a comparator 7, as Vin, and is compared with a reference voltage Vref. The reference voltage Vref determines the intensity of the output beam from the fiber coupler 4. When the voltage Vin coincides with the reference voltage Vref, the intensity of the output beam from the coupler 4 is equal to the intensity determined by the reference voltage Vref. The comparator 7 supplies an output voltage corresponding to the comparison result to the drive circuit 2. The drive circuit 2 supplies a current corresponding to the output voltage from the comparator 7 to the LED 1 to control the output light from the LED 1.

As described above, a light beam passing through the wavelength filter or color filter 3 is compared with the reference value by the comparator 7, and the drive current of the drive circuit 2 is controlled in accordance with the comparison result, so that the intensity of the output light from the LED is controlled to a predetermined intensity. In other words, a light beam passing through the filter 3 is fed back to the drive system of the LED 1, so that the voltage Vin coincides with the reference voltage Vref to set the intensity of the output light from the LED 1 to a predetermined intensity.

According to the above system, therefore, even if ambient temperature is changed, the intensity of the output beam to the outside of the device can be stabilized.

Figure 2A:
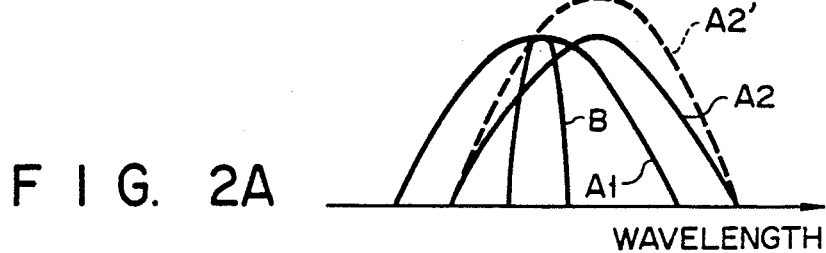
FIGS. 2A to 2C are graphs showing the spectral characteristics of light.
Figure 2B:
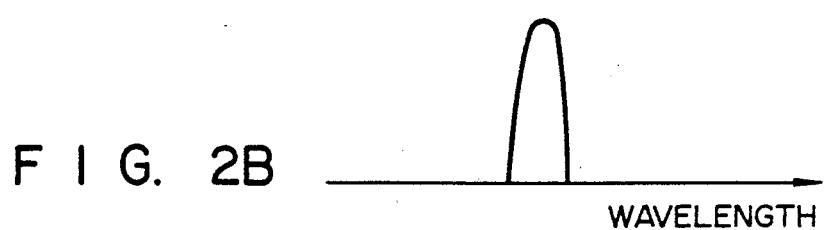
Figure 2C:
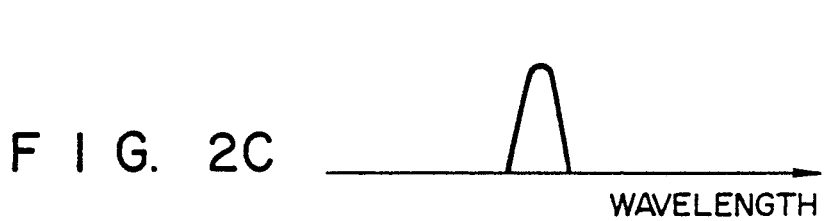

Also according to the above system, even if the wavelength characteristics of the output light of the LED 1 changes, the intensity of the output beam is kept stable. More specifically, assume that the passing band characteristics of the wavelength filter or color filter 3 is represented by a curve B as is shown in FIG. 2A, and the wavelength characteristic curve of light emitted from the LED 1 changes from a curve A1 to a curve A2 depending on a change in temperature. In this case, when the wavelength characteristics of the output light from the LED 1 are represented by the curve A1, the light beam passing through the wavelength filter 3 has the spectrum curve shown in FIG. 2B. In other words, the spectrum curve of the light beam passing through the filter 3 corresponds to the curve B of the passing band characteristics of the filter 3. However, when the wavelength characteristics of the output light of the LED 1 are represented by the curve A2, the light beam passing through the filter 3 has the spectrum curve shown in FIG. 2C. The spectrum curve of the light beam does not coincide with the curve B of the passing band characteristics of the filter 3, and the intensity of the light beam passing through the filter 3 is reduced. For this reason, if the wavelength characteristics of the output light are not compensated, the intensity of the output beam to the outside of the device is reduced. However, in this system, a light beam passing through the wavelength filter 3 is fed back to the drive system of the LED 1 to control the drive power to be applied to the LED 1. Therefore, in this system, the drive current is increased by the magnitude corresponding to the difference between the intensity of the output beam and the predetermined intensity, and the spectrum of the output beam from the LED 1 is increased, as indicated by a curve A2' shown in FIG. 2A. As a result, the spectrum curve of the beam passing through the wavelength filter 3 is substantially the same as that shown in FIG. 2B, and the intensity of the output beam to the outside of the device can be stabilized.

As described above, according to the system, since the output light characteristics and the wavelength characteristics are controlled by a feedback system, the output beam to the outside of the device can be stabilized within a short period of time after the power switch is turned on.

Note that, as the passing band of the wavelength filter or color filter 3 is smaller, the stability of the wavelength of the light beam passing through the filter 3 can be improved. Assume that the characteristic curve of the passing band of the wavelength filter 3 is represented by a curve B as is shown in FIG. 3A, and the passing band of the filter 3 is relatively broad. In this case, when the spectral characteristics of the light emitted from the LED 1 is represented by a curve A1 as is shown in FIG. 3A, the light beam passing through the wavelength filter 3 has the spectral characteristics shown in FIG. 3B. The characteristics coincides with the characteristics of the wavelength filter 3 represented by the curve B shown in FIG. 3A. However, assume that the spectral characteristics of the light emitted from the LED 1 is offset from that represented by the curve A1 to that represented by the curve A2, and the spectral characteristic is corrected by a feedback control, as represented by a curve A2' as is shown in FIG. 3A. In this case, the spectrum of the light beam passed through the filter 3 is distorted as shown in FIG. 3C, and its central wavelength is offset. In this case, if the filter 3 having a small passing band is used, the offset of the wavelength can be prevented. Thus, the filter 3 having a small passing band is preferably used.

The half-width of the emission spectrum of the LED normally falls within the range of about 100 nm to 150 nm, as far as the LED having a center wavelength of 1.3 $\mu$m or 1.55 $\mu$m is concerned. A change of the wavelength of the emission spectrum of the LED in the temperature range of $-10°$ C. to $50°$ C. is about 50 nm in maximum, and about 15 nm in minimum. In this case, the half-width of the wavelength filter 3 is preferably 20 nm or less.

When the device was driven under the temperature range of $-10°$ C. to $50°$ C. by the above-mentioned system using an LED having a center wavelength of 1.3 $\mu$m and a filter having a half-width of 20 nm, respectively, the offset of the central wavelength of the spectrum of the light beam passing through the wavelength filter or color filter 3 was 1 nm or less.

In the above embodiment, the optical fiber F0 forming the fiber coupler 4, the optical fiber F1 for guiding a light beam to the fiber coupler 4, the optical fiber F2 for guiding a light beam from the fiber coupler 4 to the outside of the device, and the optical fiber F3 for guiding a light beam to the photodiode PD5, are all the same type. For example, these optical fiber F0–F3 are all of single-mode type. Therefore, the transmission losses of light beams through the fibers F0, F1, F2, and F3 are equal to each other, and the stability of the output beam of the device is enhanced.

As described above, the fiber coupler 4 comprises the optical fiber F0. The optical fiber F0 is formed of two optical fibers f1 and f2 superposed each other at the light splitting portion where the claddings are thinner than the remaining portion of the claddings. The optical fiber F0 can be prepared by superposing two optical fibers each other, and drawing the superposed portion of the fibers in the longitudinal direction to make the claddings of the superposed portion thin so that a light passing through the fiber f1 enters the fiber f2 via the the claddings. The thinning of the claddings may alternatively be performed by scraping those portions of the claddings where the fibers are to be superposed.

FIG. 4 shows an arrangement of the comparator 7 and the drive circuit 2 used in the LED stabilizing light source device shown in FIG. 1. The comparator 7 includes npn transistors T1 to T4 and a current supply source CS, and the drive circuit 2 includes an npn transistor T5 and a load resistor R. A pair of npn transistors T1 and T2 constitute a differential amplifier. The emitter of each transistor is grounded via the current supply source CS made of, e.g., a resistor. A voltage Vin is input to the base of the transistor T1, and the base of the transistor T2 is connected to the reference voltage Vref. A pair of npn transistors T3 and T4 constitute a current mirror circuit. The collector of each transistor is connected to a power supply potential Vcc, and the gates of the transistors are connected to each other. The emitter of the transistor T4 is connected to its base and the collector of the transistor T2. The emitter of the transistor T3 is connected to the collector of the transistor T1. The collector of the transistor T1 serves as an output terminal of this amplifier, and is connected to the drive circuit 2 in the device shown in FIG. 1.

The base of the transistor T2 is connected to the reference voltage Vref, so that its collector potential is constant. The collector of the transistor T5 in the drive circuit 2 is connected to the power supply potential Vcc via the LED 1, and the emitter of the transistor 5 is grounded via a load resistor R. The gate of the transistor 5 is connected to the collector of the transistor T1 serving as the output terminal of the comparator 7.

An operation of the comparator and the drive circuit in FIG. 4 will be described below.

Assume that the spectrum of the light beam passing through the wavelength filter or color filter 3 exceeds a predetermined value determined by the reference voltage Vref. In this case, the voltage Vin is higher than the reference voltage Vref. Therefore, the transistor T1 is turned on, and its collector potential, i.e., an output potential Vout of the comparator 7 is reduced in correspondence with the input voltage Vin. Thus, the base voltage of the transistor T5 in the drive circuit 2 is reduced. For this reason, the collector current of the transistor T5, i.e., the drive current of the drive circuit 2, is decreased, and the intensity of the emission spectrum of the LED 1 is reduced. Therefore, a current flowing through the photodiode PD5 is decreased, and the voltage Vin is reduced. This cycle is repeated, and the voltage Vin coincides with the reference voltage Vref.

In contrast with the above case, assume that the spectrum of the light beam passing through the wavelength filter 3 is a predetermined value or less. In this case, the voltage Vin is lower than the reference voltage Vref. For this reason, the transistor T1 is turned off, and the output potential Vout is increased in correspondence with the input voltage Vin. Therefore, the base potential of the transistor T5 in the drive circuit 2 is increased. For this reason, the collector current of the transistor T5 is increased, and the intensity of the emission spectrum of the LED 1 is increased. Therefore, a current flowing through the photodiode PD5 is increased, and the voltage Vin is also increased. This cycle is repeated and the voltage Vin coincides wit the reference voltage Vref.

FIG. 5 shows an LED stabilizing light source device according to another embodiment of the present invention.

Those portions the same as in the device shown in FIG. 1 are designated by the same reference characters, the descriptions thereof being omitted.

In this embodiment, the light splitter 14 is formed of rod lens 151, 152, 153 and a half mirror 16. The rod lenses are focusing lenses. The light beam from wavelength filter 3 is impinged on the half mirror 16 via the rod lens $15_1$. The half mirror 16 splits the light beam into two light beams. One light beam is guided to the outside of the device via the rod lens $15_2$ and a milti-mode optical filter F11, and the other light beam is guided to the photodiode PD5 via the rod lens $15_3$ and a multi-mode optical filter F12.

In this embodiment, the guiding optical fibers F11 and F12 are both of multi-mode type. Since, the optical fibers are of the same type, the transmission losses of light beams passing therethrough are equal, and the stability of the output beam of the device is enhanced.

According to the present invention, a system wherein the light beam passing through the wavelength filter or color filter is split by the light splitter, and one split beam is fed back to the drive system of the LED to control the drive power of the LED is employed. Therefore, even if the wavelength characteristics of the output light from the LED changes, or even if the output light characteristics change, the intensity of the output beam output to the outside of the device can be kept stable. In addition, a stable output beam can be obtained within a short period of time by control using the feedback system after the power supply is turned on.

What is claimed is:

1. An LED stabilizing light source device, comprising:

an LED;
a drive circuit for driving said LED;
a wavelength filter having a predetermined passing band, for receiving output light from said LED, and passing therethrough a portion of the light whose wavelength is within said predetermined passing band;
a light beam splitter for splitting a beam of the light passing through said wavelength filter, said wavelength filter being arranged between said LED and said light beam splitter;
a beam guide member for guiding one split beam from said light beam splitter to the outside of the light source device;
a beam receiving member for receiving another split beam from said light beam splitter, and for outputting a signal corresponding to the intensity of said another split beam; and
a feedback loop for feeding back an output signal from said beam receiving member to said drive circuit.

2. A light source device according to claim 1, further comprising:
a first optical fiber for guiding said light beam passing through said wavelength filter to said light beam splitter;
a second optical fiber for guiding said another split beam from said light beam splitter to said beam receiving member;
wherein said beam guide member for guiding said one split beam to the outside of the light source device comprises a third optical fiber; and
said light beam splitter comprises a fourth optical fiber which is the same type as that of said first, second and third optical fibers.

3. The light source device according to claim 1, further comprising first and second optical fibers; and
wherein said light beam splitter comprises first, second and third rod lenses and a half mirror, said first rod lens being arranged for focusing said light beam passing through said wave-length filter onto said half mirror, said half mirror being arranged for splitting said light beam focused thereon into two split light beams, said second rod lens being arranged for focusing one split light beam onto said first optical fiber, said first optical fiber being arranged for guiding said one split light beam to the outside of the light source device, said third rod lens being arranged for focusing the other split light beam onto said second optical fiber, and said second optical fiber being arranged for guiding said other split light beam to said beam receiving member.

4. A light source according to claim 2, wherein said optical fibers are all of single-mode type.

5. A light source according to claim 3, wherein said optical fibers are all of multi-mode type.

* * * * *

UNITED STATES PATENT AND TRADEMARK OFFICE
CERTIFICATE OF CORRECTION

PATENT NO. : 4,998,043

DATED : March 5, 1991

INVENTOR(S) : UNAMI et al

It is certified that error appears in the above-identified patent and that said Letters Patent is hereby corrected as shown below:

Title page, Section [75] Inventors:  Change

"Yoshihara Unami" to --Yoshiharu Unami--.

Signed and Sealed this

Twenty-ninth Day of September, 1992

Attest:

DOUGLAS B. COMER

Attesting Officer

Acting Commissioner of Patents and Trademarks